United States Patent
Toronto et al.

(10) Patent No.: US 7,204,817 B1
(45) Date of Patent: Apr. 17, 2007

(54) FORM-IN-PLACE FOAM ORTHOPEDIC SPLINT SYSTEM

(75) Inventors: Russ Toronto, Salt Lake City, UT (US); Tom Toronto, Salt Lake City, UT (US)

(73) Assignee: Nuplyonix, L.L.C., Salt Lake City, UT (US)

( * ) Notice: Subject to any disclaimer, the term of this patent is extended or adjusted under 35 U.S.C. 154(b) by 0 days.

(21) Appl. No.: 10/785,141

(22) Filed: Feb. 24, 2004

Related U.S. Application Data

(63) Continuation of application No. 10/016,847, filed on Dec. 14, 2001, now Pat. No. 6,695,801.

(51) Int. Cl.
*A61F 5/00* (2006.01)
(52) U.S. Cl. .............................. 602/8; 602/6
(58) Field of Classification Search .............. 602/5, 602/6, 8
See application file for complete search history.

(56) References Cited

U.S. PATENT DOCUMENTS

| | | |
|---|---|---|
| 2,700,461 A | 1/1955 | Smith |
| 2,864,492 A | 12/1958 | Appala |
| 2,874,830 A | 2/1959 | Birmingham, Jr. |
| 2,961,710 A | 11/1960 | Sta |
| 3,373,741 A | 3/1968 | Hill et al. |
| 3,680,548 A | 8/1972 | Brown |
| 4,060,075 A | 11/1977 | Blomer et al. |
| 4,108,169 A | 8/1978 | Parker |
| 4,280,489 A | 7/1981 | Johnson, Jr. |
| 4,287,920 A | 9/1981 | Johnson, Jr. |
| 4,309,990 A | 1/1982 | Brooks et al. |
| 4,316,457 A | 2/1982 | Liegeois |
| 4,331,134 A | 5/1982 | Brooks et al. |
| 4,404,333 A | 9/1983 | Watanabe et al. |
| 4,433,680 A | 2/1984 | Yoon |
| 4,450,833 A | 5/1984 | Brooks et al. |
| 4,475,543 A | 10/1984 | Brooks et al. |
| 4,537,184 A | 8/1985 | Williams, Jr. |
| 4,572,171 A | 2/1986 | Wegner et al. |
| 4,573,456 A | 3/1986 | Spann |
| 4,574,793 A | 3/1986 | Lee et al. |
| 4,628,945 A | 12/1986 | Johnson, Jr. |
| 4,852,557 A | 8/1989 | Grim |
| 4,888,225 A | 12/1989 | Sandvig et al. |
| 4,968,542 A | 11/1990 | Gasper et al. |
| 5,061,555 A | 10/1991 | Edenbaum et al. |
| 5,125,400 A | 6/1992 | Johnson, Jr. |
| 5,195,946 A | 3/1993 | Li et al. |
| 5,316,545 A | 5/1994 | Cherubini |
| 5,368,549 A | 11/1994 | McVicker |
| 5,455,294 A | 10/1995 | Sheng |
| 6,695,801 B1 | 2/2004 | Toronto et al. |

*Primary Examiner*—Kim M. Lewis
(74) *Attorney, Agent, or Firm*—Kirton & McConkie; Evan R. Witt

(57) ABSTRACT

An apparatus and method for creating and using a lightweight custom-molded orthopedic appliance are disclosed. The orthopedic appliance is made up of an inner and an outer bladder containing components which, when combined by rupturing the inner bladder, react to form a rigid foam substance which may be conformed to the shape of the body part or surface in need of support, cushioning, or immobilization, and which quickly cures to form a firm, supportive brace for the affected body part.

15 Claims, 7 Drawing Sheets

FORM-IN-PLACE FOAM ORTHOPEDIC SPLINT SYSTEM

CROSS-REFERENCE TO RELATED APPLICATION

This application is a continuation of U.S. patent application Ser. No. 10/016,847, filed Dec. 14, 2001, which is now U.S. Pat. No. 6,695,801.

BACKGROUND OF THE INVENTION

1. The Field of the Invention

The present invention relates to methods and apparatus for supporting or immobilizing a body part. More specifically, the present invention relates to methods and apparatus for making and using a custom-fit, lightweight, durable orthopedic appliance (or "orthopedic splint") for use as a splint, cast, or protective pad.

2. The Relevant Technology

Many common injuries require that a body part or surface be covered with a protective dressing in order to provide support, promote healing, prevent further injury, selectively immobilize the injury, and act as a shock-absorbent buffer around it. In many such injuries, especially where the hard, durable dressings currently known in the art are used, it is generally preferred that the dressing be kept in place once it has been applied. This may be desired in order to preserve the precise setting of a bone needed for proper healing, to prevent the patient from moving or using the injured part, to enclose and protect an open wound, or to accomplish a combination of these functions.

Durable, long-lasting dressings such as these are key to medical efficiency and treatment since they can last weeks without replacement by a doctor. This saves both the patient and the doctor significant time, expense, and discomfort. Dressings of this type are often required after accidental injuries, and may also be used after some surgical procedures.

Methods and devices for stabilizing body parts and surfaces face challenges to be successful. First, since a dressing may need to be worn for extended periods, it is preferably clean; strong; resistant to wear, degradation, and rotting, etc.; waterproof, and presentable in appearance. This helps such dressings to remain clean and sterile and to protect the underlying skin from irritation and infection.

Since many emergency situations require the immobilization of a body part or surface, dressings which are quick to apply and which are strong and supportive are preferred. Further, in such emergency or first aid situations, such dressings should be easy to apply and use, thus allowing them to be employed by untrained volunteers when no trained medical personnel are available.

Finally, in an era when people are embracing lifestyles of increased physical activity, patients demand that casts and splints leave them able to participate in as many activities as possible. As a result, lightweight, small, waterproof, and strong solutions to the casting problem are advantageous.

Many methods and devices are currently known and relied on in the art for stabilizing body parts or surfaces. Prime examples of these are casts and splints including plaster casts, casts made up of synthetic resins, and splints made of resins, plastics, or metals. Many of these materials are easily conformable to the shape and size of the body part of the patient, and are able to strongly support the needed limb.

Plaster casts were formerly the most widely used form of casting. In this casting method, strips of cloth impregnated with plaster are immersed in water and carefully wound around the affected limb in layers. This mass is then painstakingly shaped and then allowed to harden over a period which may last hours to obtain a full set of the plaster. The result is a thick, solid, and often heavy cast amply capable of supporting the injured limb.

Such plaster casts are useful in many applications, but also generally suffer from disadvantages ranging from long setting periods during which the cast is not solid, and which may thus be more easily damaged, high weight and density, impermeability to X-rays, susceptibility to damage and weakening from exposure to water, and bulkiness.

Casts made of synthetic resins have become popular in recent years due to their ability to harden in a shorter period of time (relative to plaster), their lighter weight and lower density (relative to plaster), their resistance to damage from water, their permeability to X-rays, and the ability to provide them in attractive colors. These casts are popular among wearers since they are lighter and less bulky, while still retaining the needed characteristic of strength. The drawbacks of this technology include the need for wet handling and clean up or special equipment, including in some cases, equipment for producing UV rays to harden the resins, and lesser ability to form and mold the casting material.

In addition to these techniques, there is a wide range of technologies available for removably splinting a wound. These technologies allow the patient to remove the dressing when needed and replace it on their own. Many such devices involve metal or plastic supports which are pre-formed and molded within padding or foam to brace the wound. Though useful in many applications, these devices are only very poorly adaptable to the anatomy of the user, and involve increased cost, weight, and inconvenience.

Accordingly, a need exists for a lightweight orthopedic splint appliance useful for casting and splinting wounds which is easy to use, moldable to the anatomy of the patient, quick to harden without water application or external chemicals, strong, durable, waterproof, and attractive. It would be an advancement in the art to provide a self-contained orthopedic splint that does not require the use of water, gloves, or other accessories to enable use in the field or any other circumstance. Such a device is disclosed herein.

BRIEF SUMMARY OF THE INVENTION

The apparatus of the present invention has been developed in response to the present state of the art, and in particular, in response to the problems and needs in the art that have not yet been fully solved by currently available orthopedic splint and casting systems, including those referenced above.

To achieve the foregoing objects, and in accordance with the invention as embodied and broadly described herein, a form-in-place orthopedic splint system is provided. The orthopedic system includes an outer envelope having an inner face and an outer face, where the inner face has a textured surface. The outer envelope contains a liquid polyol composition which is in contact with this textured surface of the inner face. The inner envelope contains an isocyanate composition, and keeps the isocyanate segregated from the polyol in the interior of the outer envelope. This inner envelope is adapted, however, to be ruptured by a user, thus allowing the polyol and isocyanate to mix and react, causing the formation of a polyurethane foam. The inner envelope may be ruptured by many means currently known in the art including, but not limited to, pressure, tension, physical perforation, tearing, and puncturing. In many forms of the instant invention, the inner and outer envelopes may be made of a high density polyethylene or similar polymeric material. Polyethylene is notably suitable since it is an oriented plastic which may be easily torn in a predictable direction. Polyethylene is substantially water impermeable, and thus prevents water from entering the envelopes containing the reagents. The materials used in the envelopes should be substantially water impermeable to prevent the entry of water into the envelopes since water will react with isocyanate, thus fouling the reaction with the polyol composition. In some forms, the inner envelope is between about 2 and about 4 mils thick. In others, the high density polyethylene is about 2 mils thick.

In many of these embodiments of the instant invention, the outer envelope of the orthopedic splint is shaped and configured to conform to a specific body part. Specifically, the orthopedic splint may be adapted to conform to the hand, elbow, wrist, thumb, forearm, shoulder, foot, ankle, knee, leg, or other desired body parts. Those skilled in the art of constructing orthopedic splints and casts would be familiar with such known useful splint shapes, styles, and conformations.

The polyurethane foam may be adapted to have a relatively short cure time of between about 8 and 15 minutes. In some forms of the instant invention, the polyol and isocyanate are selected to yield a curing time of less than about 12 minutes. In a presently-preferred embodiment, the polyol and isocyanate reagents are selected to yield a curing time of about 10 minutes. This amount of time is sufficient to allow a medical professional to mold the cast to fit the shape of the body part or surface to be supported, while still reducing the amount of time that the patient has to remain motionless and that the doctor has to spend monitoring the patient. The exact amount of time needed for the polyurethane foam to cure is dependent upon the polyol and isocyanate chosen, and may thus be modified or adjusted to meet a chosen cure time.

In preferred embodiments of the invention, the reagents are chosen to yield a mix/cream time of about 2 minutes. During this time, the isocyanate and polyol may be easily kneaded together and mixed. After this, a rise time of approximately 4 minutes ensues in which the polyurethane foam rises and may begin to be molded to conform to the body part or surface to be supported, splinted, or cast. Following this period, a de-mold period of about four minutes ensues in which the polyurethane may still be shaped, though with more effort, and after which (at about 10 minutes from disrupting the inner envelope), the polyurethane is firm enough to provide adequate support to the body part. The reagents may also comprise coloring agents to give a color to the orthopedic splint.

The thickness of the orthopedic splint system is also carefully monitored so as to promote even strength and distribution of the foam while protecting the patient against exposure to uncomfortable or dangerous amounts of heat produced by the exothermic reaction involved in the formation of the polyurethane foam.

The polyurethane foam generated within the orthopedic splint upon mixing the polyol and isocyanate preferably has a density of between about 8 and about 12 pounds per cubic foot. In a presently-preferred embodiment of the invention, the polyurethane foam has a density of about 10 pounds per cubic foot.

The foam is adapted to harden to a useful stiffness and to adhere to the textured surface of the inner face of the inner envelope. The novel texturing of the plastic inner face dramatically increases the surface area of the inner face available to the foam for bonding, and also mechanically increases the strength of the bond formed at the interface of the foam and the envelope. A vast variety of textures may be used within the scope of the instant invention, with those being favored which maximize the surface area of the inner face. The textures are also constrained by the thickness of the outer envelope, which is preferably comprised of a high density polyethylene of between about 2 and about 4 mils in thickness. Though polyethylene is preferred for the inner and outer envelopes, materials such as Mylar, polypropylene, and others with similar properties, may be used. In addition, though the foam of the invention is preferably polyurethane, as described above, other polymeric foams which are appropriate for use with the invention may be used. The inner envelope may also be textured on its outside, or on all of its faces, and is generally comprised of a high density polyethylene of about 2 to about 4 mils in thickness.

Additionally, in some forms of the instant invention, the inner envelope is securely disposed at a fixed location within the outer envelope. In some of these, the inner envelope is secured to a corner of the outer envelope by one edge, and in others, by two edges. In others, the inside face of the outer envelope comprises part of the inner envelope. This predictability of location of the inner envelope makes the orthopedic splint system of the instant invention easy to use since the location of the needed reagent is fixed, and it may be quickly isolated and ruptured by the user.

Further, since the inner envelopes are known to often produce a structurally weakened region in the final hardened product, it is an improvement in the art to control the location of the possible weakened region so as to allow that region of the system to be placed in a region of minimum strength requirements. Indeed, in some forms of the invention where the outer envelope is shaped and adapted to conform to a specific body part, the inner envelope may be located at a position which does not interfere with the usefulness or strength of the resulting orthopedic splint device during the construction of the device. Further, the inner envelope may be comprised of a high-density polyethylene of between 2 and 4 mils in thickness. It may, as noted above, be textured on any or all faces to increase the strength of the bond of the polyurethane foam material with the envelope.

The "inner envelope" may also be placed outside of the outer envelope with a channel connecting its interior to the interior of the outer envelope. The channel may have a seal to isolate the foam producing reagents prior to activation. This seal may be frangible such that an application of pressure to the inner envelope will cause the seal to rupture, thus opening the channel into the outer envelope. The inner envelope may additionally be removable from the splint after use. This may be accomplished by using a frangible seam to connect the inner envelope to the outer envelope, as well as simply making it possible to sever the inner envelope with a sharp instrument.

In other forms, the instant invention comprises a method of stabilizing a body part or surface. A first step is obtaining an orthopedic splint of the instant invention as described above. This orthopedic splint will comprise an outer envelope having an inner face with a textured surface and an outer face which could also be textured. The outer envelope contains a polyol which is in contact with said textured surface of said inner face; and the inner envelope contains an isocyanate composition. The inner envelope is adapted to be ruptured by a user, thus allowing the polyol and composition to be mixed. A second step is the rupturing of the inner envelope and the subsequent mixing of the polyol and the isocyanate catalyst to cause the formation of a polyurethane foam. A next step is molding the orthopedic splint device to conform to the anatomical shape of the body part or surface to be supported. A following step is allowing the polyurethane foam to harden to a useful stiffness and adhere to the textured surface of the inner face within a predetermined curing time. Factors such as the predetermined curing time, the density of the foam, and the anatomical shape and characteristics of the device itself may be varied as taught herein within the scope of this method.

These and other objects, features, and advantages of the present invention will become more fully apparent from the following description and appended claims, or may be learned by the practice of the invention as set forth hereinafter.

BRIEF DESCRIPTION OF THE DRAWINGS

The invention of this application may be better understood by referring to the specific embodiments shown in the drawings which follow. The drawings depict only typical embodiments of the invention, however, and should thus not be used to limit the scope of the invention. In the drawings:

FIG. 5 is a cross-sectional schematic view of another form of the orthopedic splint of the instant invention.

DETAILED DESCRIPTION OF THE PREFERRED EMBODIMENTS

The presently preferred embodiments of the present invention will be best understood by reference to the drawings, wherein like parts are designated by like numerals throughout. It will be readily understood that the components of the present invention, as generally described and illustrated in the figures herein, could be arranged and designed in a wide variety of different configurations. Thus, the following more detailed description of the embodiments of the apparatus, system, and method of the present invention, as represented in FIGS. 1 through 4, is not intended to limit the scope of the invention, as claimed, but is merely representative of presently preferred embodiments of the invention.

DEFINITIONS

Isocyanate curing agent: as used herein, the term isocyanate curing agent includes di-, tri-, and polyfunctional organic isocyanates that have a plurality of active isocyanate functional groups and which would be suitable for reacting with a polyol to form a polyurethane foam for use in the orthopedic splint of the instant invention.

Polyol: as used herein, the term polyol connotes an alcohol containing a plurality of reactive hydroxyl functional groups.

Orthopedic splint: as used herein, the term orthopedic splint is used to denote devices which support, splint, or cast body parts or surfaces to stabilize them, immobilize them, cover them, or protect them from further injury or from contamination.

DETAILED DESCRIPTION

Figure 1:
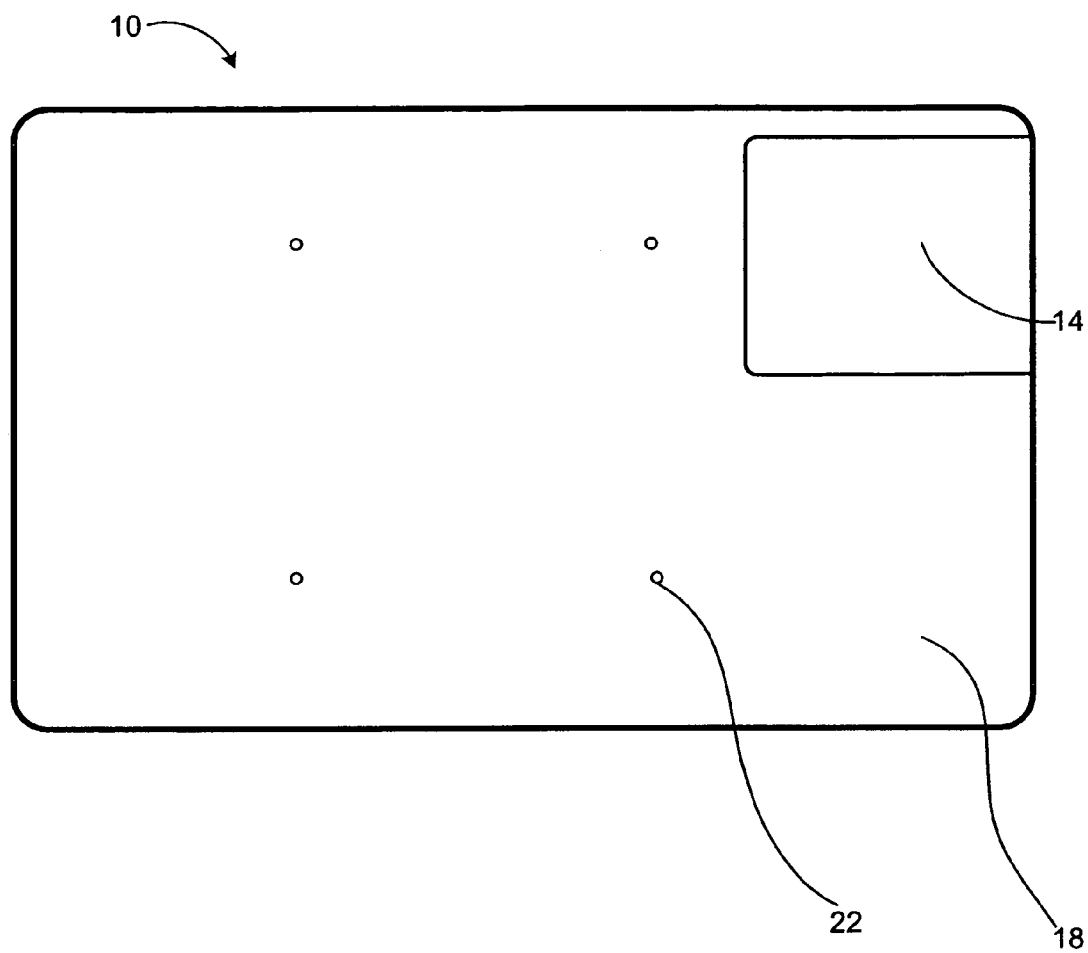
FIG. 1 is a top schematic view of the orthopedic splint of the instant invention.

Referring now to attached FIG. 1, a top schematic view of a form of the foam orthopedic splint system 10 of the instant invention is shown. Specifically, the orthopedic splint system 10 is shown comprising an outer envelope 18 and an inner envelope 14. These envelopes act as partitions to temporarily separate the reactants needed to form a polyurethane foam.

The outer envelope 18 is uniquely adapted to provide flexibility, durability, and strength. The outer envelope is preferably constructed of a material such as polyethylene that allows flexibility in order to allow it to conform to the body part or surface. In addition, the material should be strong before use as a splint to safely and effectively house the polyol needed for the reaction to form polyurethane foam. In some embodiments the envelope is preferably composed of a high density polyethylene ("HDPE") of about 16-pound strength, and being between about 2 and about 4 mils thick. In a preferred embodiment, the high density polyethylene is about 2 mils thick. In the instant invention, the inner face of the outer envelope is textured, as is shown in FIGS. 4, 5, 6, and 7. Many advantages are realized as a result of this unique characteristic.

First, the textured inner face of the outer envelope gives dramatically-increased adhesive strength to the bond formed between the envelope and the polyurethane foam generated within the envelope. The texturing of this surface dramatically increases the surface area of this inner face, thus giving a much larger area for the polyurethane foam to bond to. This significantly increases the tensile strength of the bond and the structural integrity of the orthopedic splint as a whole.

In certain storage scenarios, due to the fluid nature of the contents of the outer envelope, the polyol contents may aggregate in one area of the outer envelope, thus allowing other areas of the inner face to contact each other. This contact may cause the inside faces to adhere to each other—an event which would prevent proper distribution of the foam within the envelope, thus rendering it less useful due to uneven and improper distribution of the foam. The texturing of the surface preserves the usability of the device by inhibiting opposite sides of the inner face from adhering to each other.

The textured surface of the inside face of the outer envelope of the instant invention also promotes the strength of the bond by promoting "skinning" in the polyurethane. The polyurethane foam's strength and low density may be attributed in part to the gas bubbles which make it a foam. If present at the interface between the foam and the envelope, however, these bubbles may weaken the bond between the foam and the envelope by reducing the surface area at which the foam is contacting the envelope. The surface texturing of the inside face of the outer envelope, however, reduces this problem by promoting "skinning"—the formation of a thin polyurethane layer of up to about 1 millimeter in thickness. This polyurethane "skin" further strengthens the integrity of the foam/envelope bond.

The inner envelope differs from the outer envelope in that it is uniquely adapted to be ruptured so as to release the isocyanate it contains into the reservoir of polyol contained within the outer envelope, thus initiating the chemical reaction that forms the polyurethane foam. This inner envelope may be adapted to be ruptured in a large variety of ways, including mechanical and chemical means. This may include using a seam engineered to rupture in response to a given pressure on an edge of the envelope; an indentation, perforation, or other feature on a surface of the envelope to make it susceptible to designed rupture; a partially cut tab on the edge of the envelope to aid in tearing; or folded forms which rupture/tear the inner envelope upon the unfolding of the non-activated orthopedic splint. Also, the inner envelope is preferably constructed of a durable material which resists certain pressures in order to separate the isocyanate from the polyol. It is also further preferably constructed of a material which may be engineered to produce a seam or surface weakness (such as an indentation, perforation, etc.) which may rupture in a predictable and controlled manner in response to a pressure applied by a user. In some presently-preferred embodiments, the inner envelope 14 is composed of high density polyethylene ("HDPE") of about 16-pound strength, and being between about 2 and about 4 mils thick. As briefly mentioned above, polyethylene is substantially water impermeable and, being an oriented polymer film, can be torn in a predictable fashion.

The inner envelope of the orthopedic splint device of the instant invention may be fixed in position relative to the outer envelope. In some forms, the inner envelope is fixed in a corner of the outer envelope. This may involve attachment at one or more edges of the outer envelope. This novel configuration provides benefits over the prior art by controlling the location of the inner envelope. The inner envelope may create a weakened region in the orthopedic splint. By locating the inner envelope in a fixed position relative to the outer envelope, the instant invention allows the user to identify and control the location of any prospective weak spot. The orthopedic splint device may be designed and used to avoid putting the weakened region in a location on the body part or surface which will be subject to strong forces which could cause damage to the orthopedic splint device. Additionally, the inner envelope 14 may be constructed of paraffin so as to provide an effective vapor barrier for the isocyanates, while being convenient to rupture.

Figure 2:
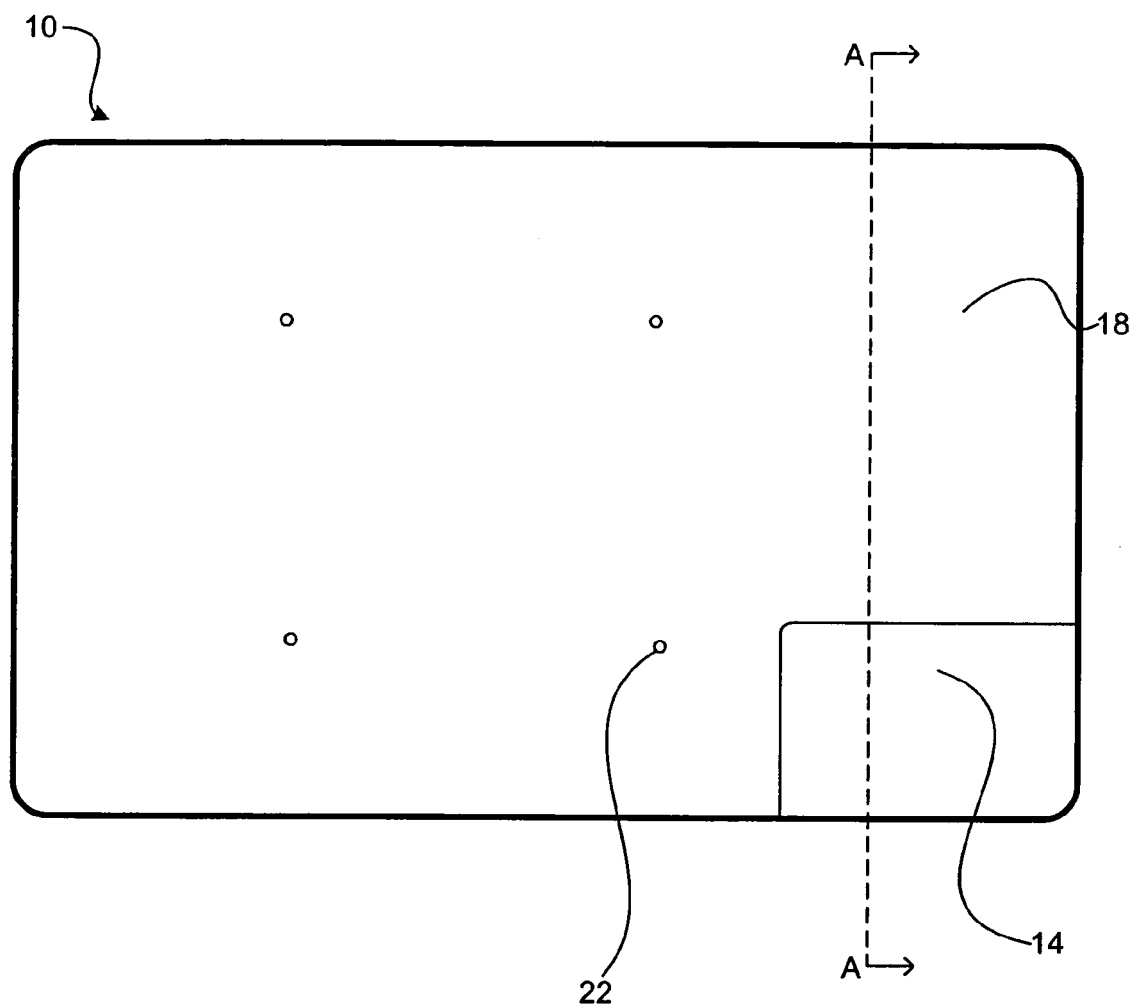
FIG. 2 is a top schematic view of a second form of the orthopedic splint of the instant invention.
Figure 3:
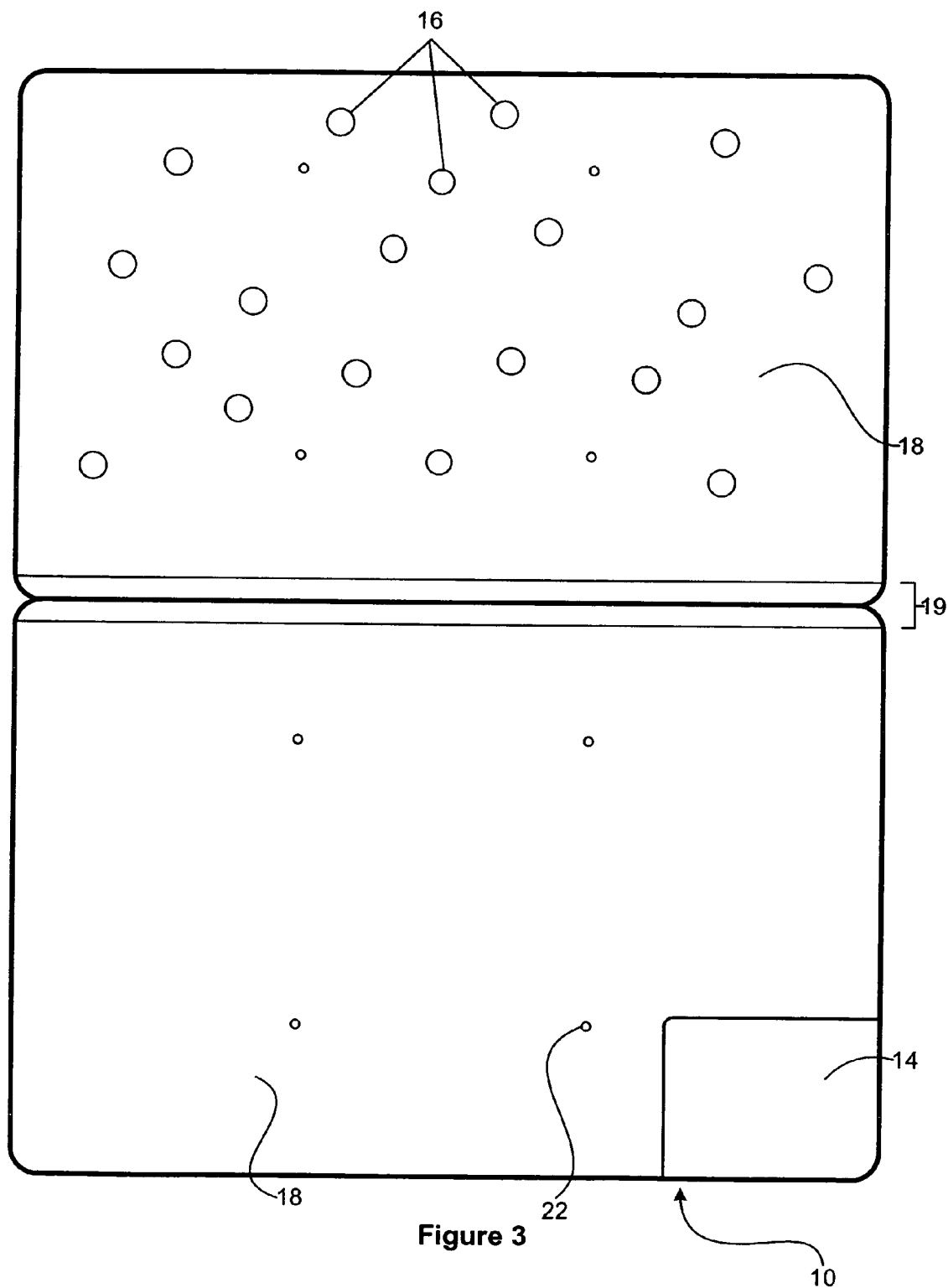
FIG. 3 is a schematic view of a third form of the orthopedic splint of the instant invention.

FIG. 2 shows a form of the orthopedic splint device of the instant invention in which the inner envelope 14 is mounted in a corner of the outer envelope 18. FIG. 3 shows another form of the orthopedic splint device 10 within the scope of the instant invention. This form comprises two outer envelopes 18 shown connected by a hinge region 19, which may be constructed in many different ways familiar to one of skill in the art. One convenient method of constructing hinge region 19 is by bonding or sealing polymer sheets together to form a seam. In the form shown, the envelopes 18 are completely separate, and thus each has a separate source of isocyanate curing agent. In the form shown in FIG. 3, one envelope 18 has an inner envelope 14 and the other envelope 18 has isocyanate capsules 16. These capsules may comprise an encapsulating agent and isocyanate curing agent. The encapsulating agent here is analogous to the inner envelope 14 in that it segregates the isocyanate from the polyol, and is rupturable. The type of encapsulating agent is chosen to provide an effective vapor barrier for the isocyanate to preserve its ability to react with the polyol, and keep it separate from the polyol. Encapsulating agents increase the useful shelf life of the orthopedic splint of the instant invention by creating a more perfect vapor barrier to encapsulate the isocyanate. In addition, however, the encapsulating agent must be one which may be ruptured to release the encapsulated isocyanate upon activation of the device. This may be accomplished by using methods such as manual crushing of the capsules or by using a roller. One preferred encapsulating agent is paraffin.

Embodiments such as that shown in FIG. 3 may exist in which the envelopes are not completely separate, but only partially compartmentalized. Further, forms may exist within the scope of the instant invention which comprise more than 2 outer or inner envelopes disposed in series. Further embodiments may be made where the orthopedic splint comprises three outer envelopes and at least one inner envelope. Additionally, some forms of the instant invention may be made which comprise only one outer envelope, but multiple inner envelopes or capsules containing isocyanate.

Figure 4:
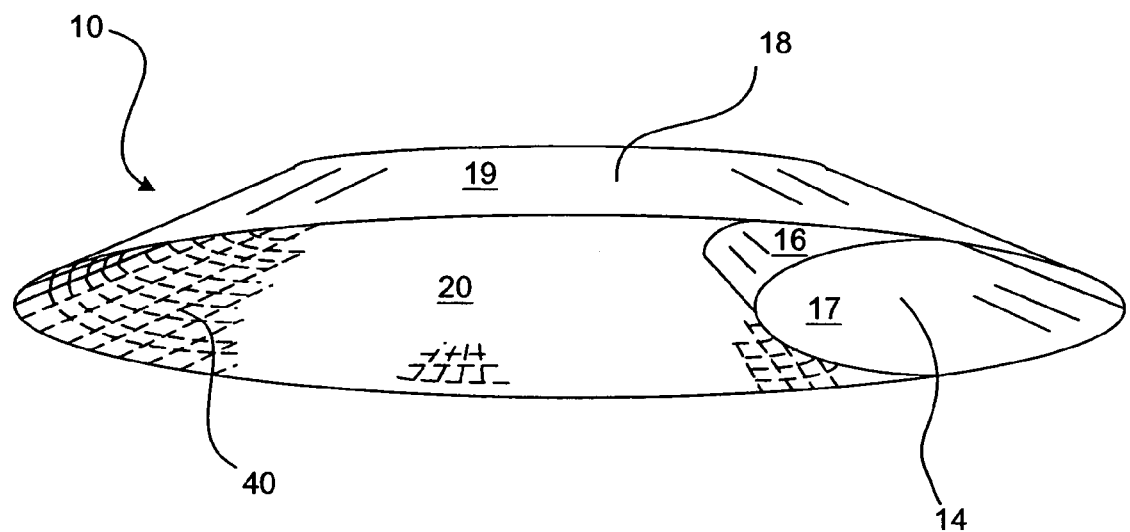
FIG. 4 is a cross-sectional schematic view of the form of FIG. 2 at line AA.

FIG. 4 is a schematic cross-sectional view of the embodiment of FIG. 2 taken along line AA. In this view, the orthopedic splint 10 has an outer envelope 18 with an outer face 19 and an inner face 20. The orthopedic splint also has an inner envelope 14 with an outer surface 16 and an inner surface 17. In such embodiments, the inner and outer envelopes may be constructed of strong, flexible materials which allow the splint to be conformed to a body part or surface. In many embodiments of the invention, this material is HDPE, and has a texture 40. The envelopes may be made according to many methods known in the art, including folding a single sheet of material and sealing it on three sides, or sealing two pieces of material on four edges. In some forms of the invention, the inner and outer envelopes share at least one seam. In others, the inner and outer envelopes may share at least two seams.

Figure 5:
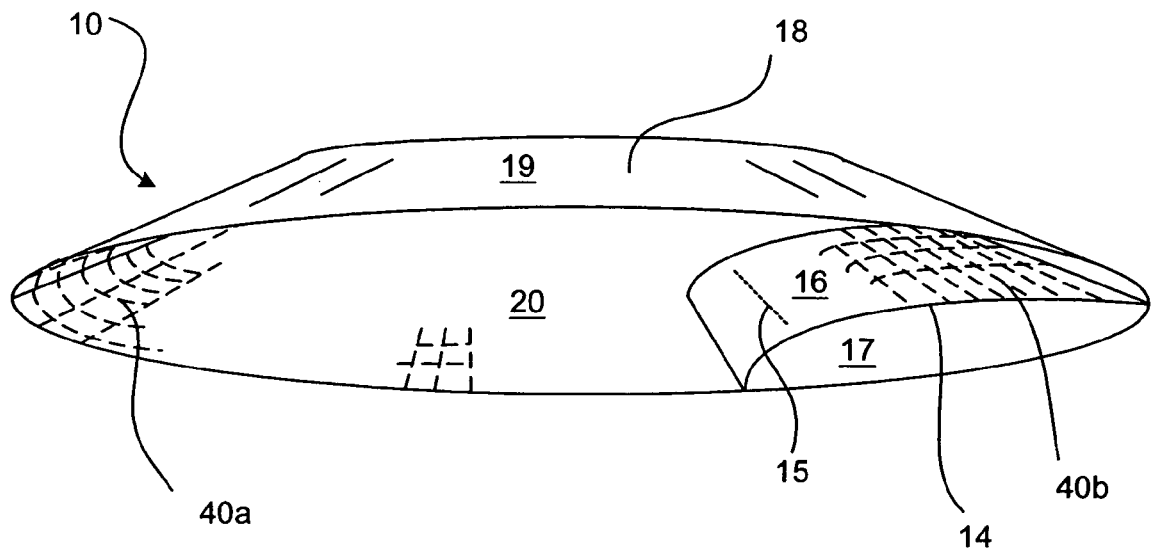
FIG. 5 is a cross-sectional schematic view of an form similar to that portrayed in FIG. 2 at line AA.

FIG. 5 shows a cross-sectional view of an embodiment in which the inner envelope is fused on one face to an inner face 20 of the outer envelope 18. In this embodiment the outer face 16 of the inner envelope 14 has a texture 40b, similar or identical to the texture 40a of the outer envelope to confer the benefits discussed above to the bond between the inner envelope 14 and the polyurethane foam formed when the contents of the inner and outer envelopes are mixed. This embodiment further demonstrates an engineered surface weakness, 15, which is constructed to retain the isocyanate during storage, but be ruptured upon the application of a pressure by a user to release the isocyanate.

Figure 6:
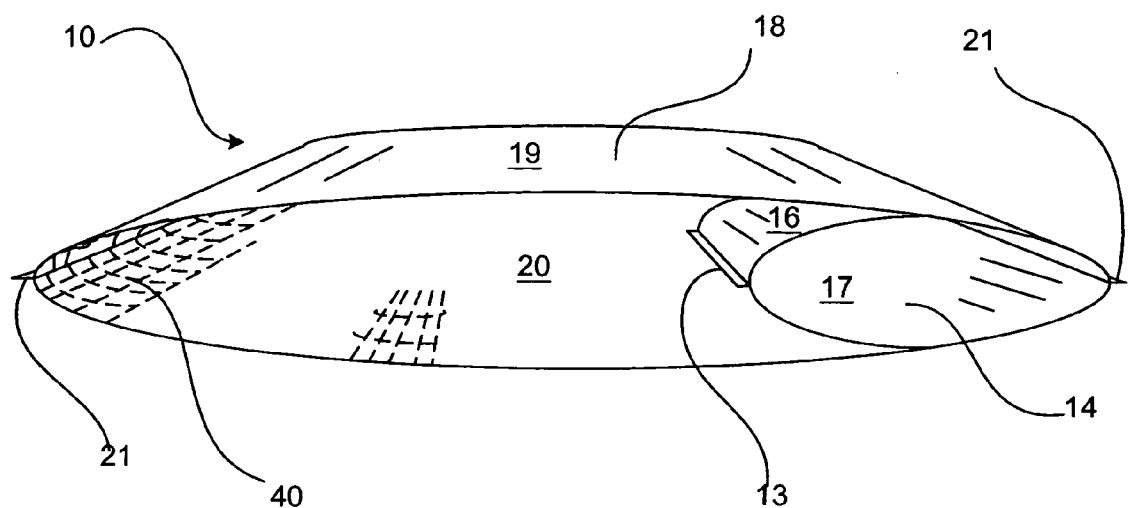
FIG. 6 is a cross-sectional schematic view of yet another form of the orthopedic splint of the instant invention.

FIG. 6 shows another cross-sectional view of an embodiment of the instant invention 10 having an outer envelope 18 with a texture 40 and an inner envelope 14. This embodiment shows an orthopedic splint constructed by sealing two sheets of plastic at their edges to form the outer envelope, thus creating seams 21. The inner envelope may similarly be formed by sealing two sheets of plastic at their edges, forming seam 13. In this embodiment, the inner envelope and the outer envelope share at least one seam, as illustrated. In this embodiment, seam 13 is engineered to retain the isocyanate inside the inner envelope during storage, and to rupture upon the application of pressure by a user, thus releasing the isocyanate.

Figure 7:
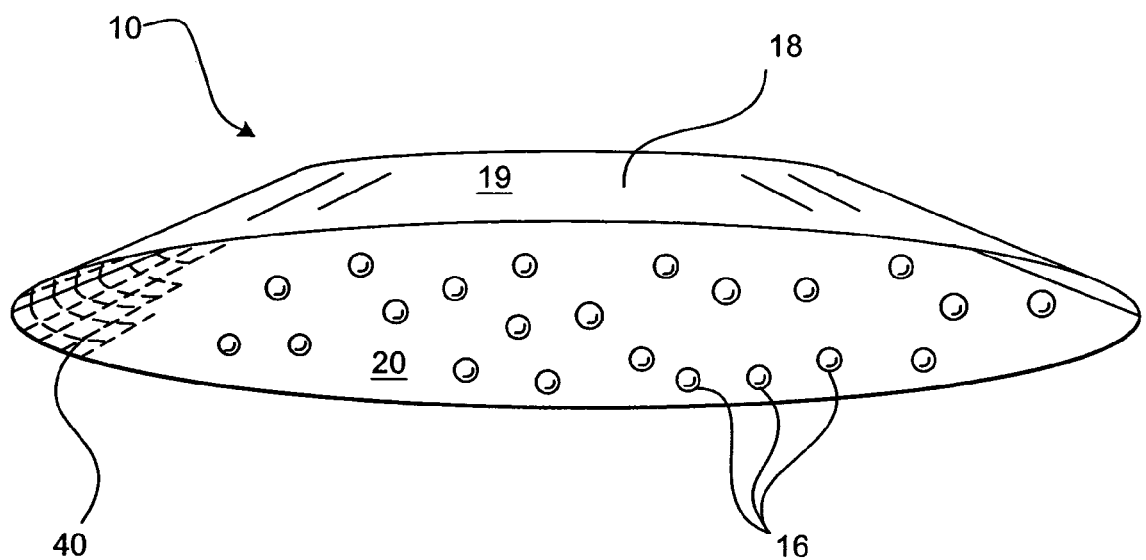
FIG. 7 is a cross-sectional schematic view of still another form of the orthopedic splint of the instant invention.

FIG. 7 shows an additional cross-sectional view of an embodiment of the instant invention 10 comprising an outer envelope 18 having an inner surface 20 with a texture 40 and an outer surface 19; and isocyanate capsules 16. These isocyanate capsules are as defined above in reference to FIG. 3, and comprise an encapsulating agent surrounding isocyanate. In this embodiment, as above, the invention is activated by rupturing the individual isocyanate capsules by pressure applied by a user, including pressure applied by means including squeezing or using a roller.

The thickness of the orthopedic splint device of the instant invention is important for a variety of different reasons. First, uniform thickness provides uniform strength and weight to the orthopedic splint, where imbalances would render some portions of the device weak, and others heavy. Further, since the formation of polyurethane is an exothermic process, the thickness of the device is proportionate to the amount of heat given off during the polyurethane curing reaction as the device is molded to fit the body part or surface. Excessive heat can burn the user or be uncomfortable. In some preferred embodiments, the temperature of the device when the polyurethane foam is curing is less than about 104° F.

Orthopedic splint device thickness may be controlled by a variety of methods known in the art. The thickness of the orthopedic splint device is preferably from about 0.8 and about 1 cm. Referring now again to FIGS. 1 and 2, spot welds 22 are shown. The spot welds portrayed are exemplary of the many types of welds which may be used to regulate the thickness of the orthopedic splint when filled with foam. In addition to this, welds may be used to partially or completely compartmentalize the outer envelope. Additionally, the shape and configuration of the outer envelope may be altered to include features such as pleats, seams, etc., to control the thickness of the orthopedic splint device.

The reactants contained within the inner and outer envelopes of the instant invention are selected to keep reaction temperatures within acceptable levels, deliver a rigid orthopedic splint product, and have a cure time short enough that patients would be able to remain still and that a medical professional would be able to attend to the curing of the orthopedic splint. Persons skilled in the polyurethane foam art are familiar with combinations of different polyol and isocyanate curing agent reactants that may be varied to achieve the mix/cream, rise, and de-mold times described herein. In preferred embodiments of the invention, the reagents present in the individual envelopes are chosen to yield a mix/cream time of about 2 minutes. During this time, the isocyanate and polyol may be easily kneaded together and mixed. After this, a 4-minute rise time ensues in which the polyurethane foam rises and may begin to be molded to conform to the body part or surface to be supported, splinted, or cast. Following this period, a de-mold period of about four minutes ensues in which the polyurethane may still be shaped, though with more effort, and after which (at about 10 minutes from disrupting the inner envelope), the polyurethane is firm enough to provide adequate support to the body part. The reagents may also comprise coloring agents to give a color to the orthopedic splint. Indeed, other chemical components which add useful properties to the polyurethane, such as agents which improve its strength, bonding ability, or molding ability, as well as components which could change the heat output of the orthopedic splint of the instant invention, could easily be incorporated into the instant invention without exceeding its scope.

In a preferred embodiment of the invention, the reactants contained within the inner envelope include an isocyanate curing agent. Currently preferred isocyanate curing agents include m-tetramethyl xylene diisocyanate (TMXDI), isophorone diisocyanate (IPDI), dimeryl diisocyanate (DDI), toluene 2, 4,-diisocyanate (TDI), and 4, 4'-diphenylmethane diisocyanate. Persons skilled in the polyurethane or polymeric foam art will appreciate that other isocyante curing agents may be used herein. In one formulation, isocyanate includes 50–75% 4, 4'-diphenylmethane diisocyanate in combination with a smaller percentage of modified MDIs ("methane diisocyanates") and other oligomers.

Additionally, in a preferred embodiment of the invention, the reactants contained within the outer envelope include a polyol or mixtures of polyols and other additives, catalysts or modifiers. In one formulation, the outer envelope contains a commercially available polyol mixture sold under the tradename Aquathane. Aquathane generally comprises polyether resins, polyester resins, tertiary amine catalyst, diethylene glycol, glycerine, and polyether modified siloxane. In one formulation, aquathane includes 50–95% polyether resins, 0–20% polyester resins, 0.5–2.5% tertiary amine catalyst, 0–10% diethylene glycol, 0–5% glycerine, and less than 1% polyether modified siloxane. The aquathane/isocyanate system provides a suitable polyurethane foam system at a low cost without the requirement of chemical permits or complicated handling. Persons skilled in the art of polymeric foams will understand that many reagent combinations will yield many combinations which may be used within the scope of the invention without departing from it.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. An orthopedic splint comprising:
   at least one outer envelope having an inner face and an outer face, said inner face having a textured surface, and said outer envelope containing a polyol, wherein the outer envelope is substantially impermeable to water and to said polyol; and
   at least one inner envelope containing isocyanate, said inner envelope being adapted to be ruptured, wherein rupturing the inner envelope allows the polyol and isocyanate to be mixed to form a polyurethane foam, said polyurethane foam being adapted to harden and adhere to the textured surface of the inner face within a curing time.

2. The orthopedic splint of claim 1, wherein the inner envelope is securely disposed at a fixed location to the outer envelope.

3. The orthopedic splint of claim 1, wherein the curing time is less than about 12 minutes.

4. The orthopedic splint of claim 3, wherein the curing time is about 10 minutes.

5. The orthopedic splint of claim 1, wherein the orthopedic splint comprises two outer envelopes and at least one inner envelope.

6. The orthopedic splint of claim 1, wherein the orthopedic splint comprises three outer envelopes and at least one inner envelope.

7. The orthopedic splint of claim 1, wherein the isocyanate is encapsulated by an encapsulating agent.

8. The orthopedic splint of claim 7, wherein the encapsulating agent is paraffin.

9. The orthopedic splint of claim 1, wherein the inner and outer envelopes comprise a high density polyethylene.

10. The orthopedic splint of claim 9, wherein the high density polyethylene is between about 2 and 4 mils thick.

11. The orthopedic splint of claim 1, wherein the inner envelope comprises paraffin.

12. The orthopedic splint of claim 1, wherein the outer envelope is shaped and configured to conform to a specific body part.

13. The orthopedic splint of claim 1, wherein said polyurethane foam has a density of between about 8 and about 12 pounds per cubic foot.

14. The orthopedic splint of claim 1, wherein said polyurethane foam has a density of about 10 pounds per cubic foot.

15. The orthopedic splint of claim 1, wherein the inner and outer envelopes comprise a high density polyethylene having a thickness between about 2 and 4 mils thick.

* * * * *